US00PP21587P2

(12) United States Plant Patent
Sorenson

(10) Patent No.: US PP21,587 P2
(45) Date of Patent: Dec. 21, 2010

(54) ***GAILLARDIA* PLANT NAMED 'BETHSHEBALEE'**

(50) Latin Name: *Gaillardia grandiflora*
Varietal Denomination: Bethshebalee

(76) Inventor: Jean Sorenson, 6110 Old East Rd., Victoria, BC (CA) V8Y 1V6

( * ) Notice: Subject to any disclaimer, the term of this patent is extended or adjusted under 35 U.S.C. 154(b) by 0 days.

(21) Appl. No.: 12/380,502

(22) Filed: Feb. 27, 2009

(51) Int. Cl.
*A01H 5/00* (2006.01)

(52) U.S. Cl. ..... Plt./431

(58) Field of Classification Search ..... Plt./431
See application file for complete search history.

*Primary Examiner*—Susan B McCormick Ewoldt

(57) ABSTRACT

A new and distinct *Gaillardia grandiflora* cultivar named 'Bethshebalee' is disclosed, characterized by full flowers, with many petals, and producing many flowers per plant. The new variety is a *Gaillardia*, suitable for outdoor and container gardens.

1 Drawing Sheet

Figure 1:
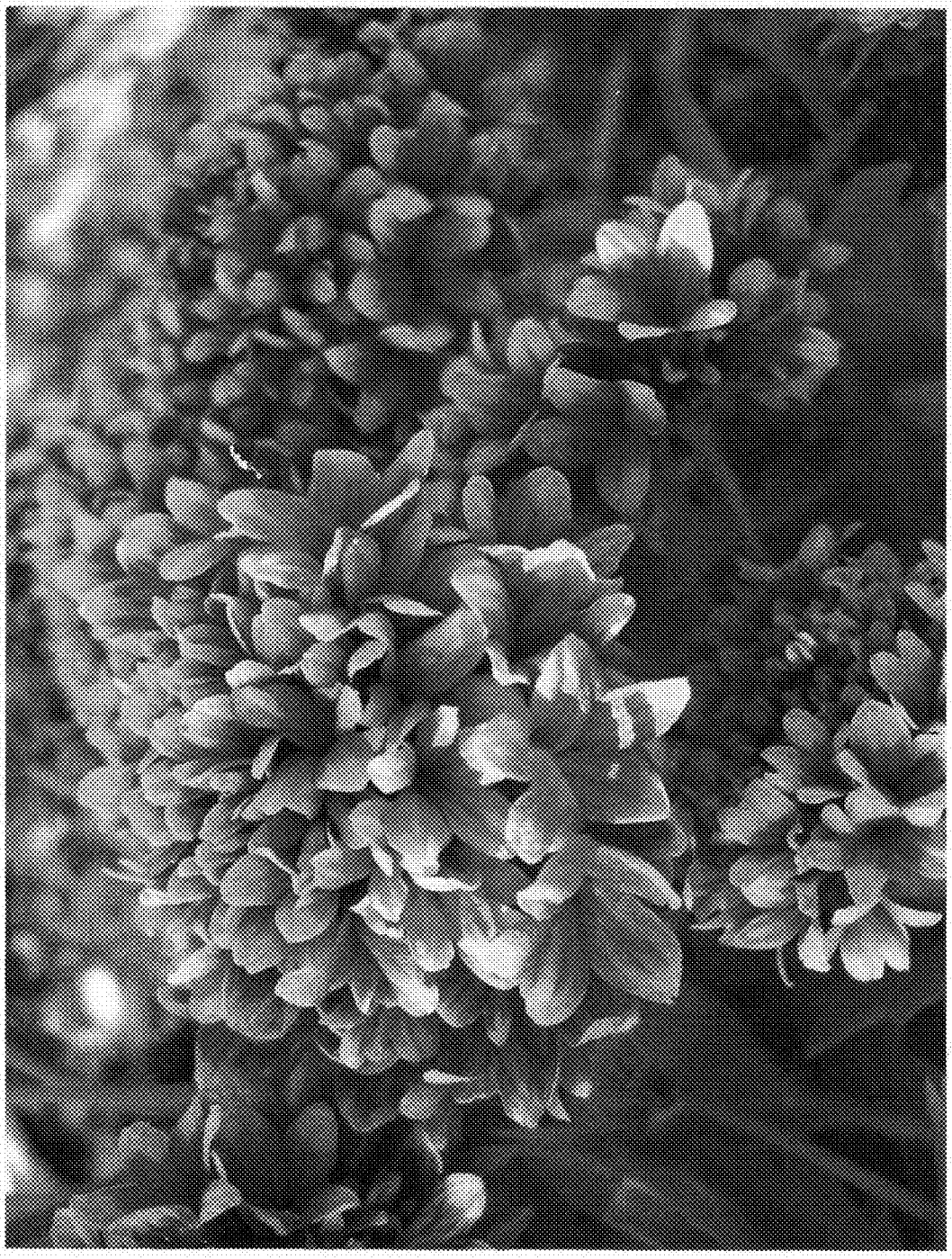

Latin name of the genus and species: *Gaillardia grandiflora.*

Variety denomination: 'BETHSHEBALEE'.

BACKGROUND OF THE INVENTION

The new variety was discovered in a garden, by the inventor, as a naturally occurring whole plant mutation in a grouping of more than 100 plants of the parent, an unknown variety of *Gaillardia grandiflora* unpatented, in the United States. It was discovered by Jean Sorenson in 2007 at Victoria, BC, Canada.

Asexual reproduction of the new cultivar 'Bethshebalee' by vegetative cuttings was performed in British Columbia and the Netherlands during the summer of 2007 and has shown that the unique features of this cultivar are stable and reproduced true to type in successive generations.

SUMMARY OF THE INVENTION

The cultivar 'Bethshebalee' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Bethshebalee' These characteristics in combination distinguish 'Bethshebalee' as a new and distinct *Gaillardia* cultivar:

1. The new variety has a much fuller flower than other perennial type *Gaillardias.*
2. The new variety produces more flowers than other perennial type *Gaillardias.*

Plants of the new cultivar 'Bethshebalee' are similar to plants of the parent variety, *Gaillardia grandiflora* in most horticultural characteristics; however, 'Bethshebalee' produces flowers with many more petals, and more flowers per plant than the parent variety.

BRIEF DESCRIPTION OF THE PHOTOGRAPH

The accompanying photograph in FIG. 1 illustrates in full color a typical flowering plant of 'Bethshebalee' grown outdoors in the Netherlands. The pot size is a commercial 9 cm container. The plant shown is approximately 1 year old. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'Bethshebalee' plants grown outdoors in the Netherlands from Fall 2006 to Fall 2007. The growing temperature ranged from 5° C. to 17° C. at night to 14° C. to 28° C. during the day. Measurements and numerical values represent averages of typical flowering types.

Botanical classification: *Gaillardia grandiflora* cultivar 'BETHSHEBALEE'.

PROPAGATION

Time to rooting: 7 to 10 days at approximately 18° C.
Root description: Fine, fibrous.

PLANT

Growth habit: Hardy herbaceous perennial.
Height: Approximately 23.5 cm.
Blooming period: Naturally blooming Summer to early Fall.
Plant spread: Approximately 25 cm.
Growth rate: Moderate.
Branching characteristics: Basal branching, moderately free branching.
Length of lateral branches: Approximately 13.5 cm.
Diameter of lateral branches: Approximately 0.2 cm.
Quantity of lateral branches: Approximately 11.
Texture of lateral branches: Densely covered with strigose hairs.
*Hair length.*—Average 0.15 cm.
*Hair color.*—Near RHS White N155A.

Color of lateral branches: Near RHS Yellow-Green 144C.
Aspect: Approximately 35° Angle.
Number of leaves per lateral branch: Approximately 18.
Age of plant described: Approximately 1 year from an unrooted cutting.

FOLIAGE

Leaf:
*Arrangement.*—Alternate, simple.
*Average length.*—Approximately 6.2 cm.
*Average width.*—Approximately 2.0 cm.
*Shape of blade.*—Obovate.
*Apex.*—Broadly acute.
*Base.*—Long attenuate.
*Attachment.*—Sessile.
*Margin.*—Serrate, for most of plant. Lowermost leaves are entire.
*Texture of top surface.*—Covered in dense strigose hairs.
*Texture of bottom surface.*—Covered in dense, strigose hairs. Both Sides Hair length: Average 0.02 cm. Both Sides Hair color: Near RHS Green-White 157D.
*Leaf internode length.*—Approximately 0.9 cm.
*Color.*—Young foliage upper side: Near RHS Green 138A and 143A. Young foliage under side: Near Green 138A and 143A. Mature foliage upper side: Near Green 138B. Mature foliage under side: Near Green 138B.
*Venation.*—Type: Pinnate. Venation color upper side: Near Yellow-Green 145B. Venation color under side: Near Green 138B.
Petiole: Not present.
Other foliage characteristics:
*Fragrance.*—Foliage has a chrysanthemum-like scent when crushed.

FLOWER

Bloom period: Naturally blooming continuously from Summer to mid-Fall.
Bud:
*Bud shape.*—Flattened globular.
*Bud length.*—Approximately 0.9 cm.
*Bud diameter.*—Approximately 1.9 cm.
*Bud color.*—Near RHS Green 143C. Yellow center near Yellow-Green 144C.
Inflorescence:
*Form.*—Terminal capitulum consisting of ray florets and disc florets.
Flower:
*Diameter of entire flower.*—Approximately 4.9 cm.
*Depth of flower.*—Approximately 2.1 cm.
*Disc diameter.*—Approximately 3.2 cm.
*Receptacle shape.*—Rounded.
*Receptacle height.*—Average 0.3 cm.
*Receptacle diameter.*—Average 0.4 cm.
*Receptacle color.*—Near RHS White 155A.
*Quantity of inflorescences per lateral stem.*—1.
*Quantity of open inflorescences and buds per plant.*—Average 11.
*Longevity.*—Average 3 weeks without significant fading or aging. Persistent.
Ray florets:
*Arrangement.*—Rotate in a single whorl.
*Aspect/orientation.*—Flat outward to slightly upright, approximately 5° angle.
*Shape.*—Campanulate, individually fused.
*Number of ray florets.*—Avg. 17.
*Length.*—Approximately 2.1 cm.
*Width.*—Approximately 1.5 cm, at diameter of campanulate shape.
*Apex shape.*—Praemorse(looking like 5 separate but fused petals.).
*Base.*—Cuneate, fused into a tubular shape.
*Margin.*—Entire.
*Texture.*—Smooth, slightly ribbed lengthwise.
Color:
*Ray florets.*—Upper surface at first opening: Near RHS Red 53A, tip Yellow 13B. Upper surface at maturity: Near RHS Red 46A, tips Yellow 13A. Upper surface at fading: Not fading, same as mature coloration. Under surface at first opening: Near RHS Orange-Red N34A, tips Yellow 11A. Under surface at maturity: Near RHS Orange-Red N34A, tips Yellow 11A. Under surface at fading: Not fading, same as mature coloration.
*Disc florets.*—Number of disc florets: Average 100. Arrangement: Spirally placed on disc. Length: Approximately 1 cm. Width: Approximately 0.5 cm. Shape: Trumpet-shaped. Margin: Upper 30% entire, lower 70% fused into a tube. Apex: Acute. Base: Fused. Texture: Smooth, slightly glossy.
Color:
*Disc florets.*—Upperside at first opening: Near RHS Red 53A, tips Yellow 13B. Upperside at maturity: Near RHS Red 46A, tips Yellow 13A. Underside at first opening: Near RHS Orange-Red N34A, tips yellow 11A. Underside at maturity: Near RHS Orange-Red N34A, tips yellow 11A.
Fragrance: Sweet, somewhat chrysanthemum-like.

PHYLLARIES/INVOLUCAL BRACTS

*Arrangement.*—Rotate in 2 rows.
*Number.*—Approximately 24.
*Length.*—Approximately 1.5 cm.
*Width.*—Approximately 0.4 cm.
*Shape.*—Lanceolate.
*Apex.*—Acute.
*Base.*—Cuneate.
*Margin.*—Entire, with short hairs directly on margin.
*Texture.*—Dull, covered with short hairs.
*Color.*—Inside color near RHS Green 143B, Base near Yellow-Green 144B. Outside color near RHS Green 143B, Base near Yellow-Green 144B.

PEDUNCLE

*Length.*—Average 13.0 cm. Only terminal peduncles present.
*Width.*—Average 0.2 cm.
*Texture.*—Slightly glossy, densely covered with strigose hairs.
*Color.*—Near RHS Yellow-Green 144C.

REPRODUCTIVE ORGANS

Not detected.

OTHER CHARACTERISTICS

Disease resistance: Neither resistance nor susceptibility to diseases or pests has been observed in this variety.

Drought tolerance and temperature tolerance: Extremely hardy perennial. Hardy to −25° C. Upper temperature tolerance to at least 35° C. Some drought tolerance, established plants can tolerate infrequent summer waterings.

Fruit/seed production: Fruit and seed production have not been observed in the new cultivar.

What is claimed is:

1. A new and distinct cultivar of *Gaillardia* plant named 'Bethshebalee' as herein illustrated and described.

* * * * *